United States Patent [19]

Gericke et al.

[11] Patent Number: 5,461,066
[45] Date of Patent: Oct. 24, 1995

[54] 4-AMINO-1-PIPERIDYLBENZOYL GUANIDINES

[75] Inventors: Rolf Gericke, Seeheim; Manfred Baumgarth, Darmstadt; Dieter Dorsch, Ober-Ramstadt; Norbert Beier, Reinheim; Klaus-Otto Minck, Ober-Ramstadt; Ingeborg Lues, Darmstadt, all of Germany

[73] Assignee: Merck Patent Gesellschaft mit beschrankter Haftung, Darmstadt, Germany

[21] Appl. No.: 385,790

[22] Filed: Feb. 9, 1995

[30] Foreign Application Priority Data

Feb. 10, 1994 [DE] Germany .................. 44 04 183.7

[51] Int. Cl.⁶ .................. C07D 401/12; C07D 211/98; A61K 31/445
[52] U.S. Cl. .................. 514/329; 546/223; 546/224
[58] Field of Search .................. 546/223, 224; 514/329

[56] References Cited

U.S. PATENT DOCUMENTS

| | | | |
|---|---|---|---|
| 5,091,394 | 2/1992 | Englert et al. | 514/331 |
| 5,292,755 | 3/1994 | Englert et al. | 514/331 |
| 5,296,485 | 3/1994 | Lubish et al. | 546/223 |
| 5,364,868 | 11/1994 | Englert et al | 514/331 |
| 5,395,826 | 3/1995 | Naumann et al | 514/107 |

FOREIGN PATENT DOCUMENTS

| | | | |
|---|---|---|---|
| 0416499 | 3/1991 | European Pat. Off. | 514/331 |
| 2,106,613 | 3/1994 | Canada | |

OTHER PUBLICATIONS

Ishida, Chemical Abstracts, vol. 63, No. 10, Nov. 8, 1965, pp. 13718–13719.

*Primary Examiner*—C. Warren Ivy
*Assistant Examiner*—Zinna N. Davis
*Attorney, Agent, or Firm*—Millen, White, Zelano & Branigan

[57] ABSTRACT

4-amino-1-piperidylbenzoylguanidines of the formula I

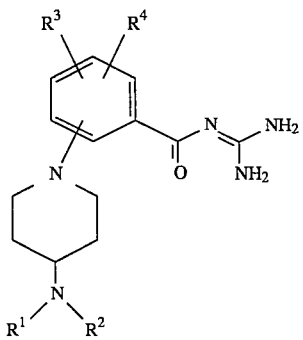

in which $R^1$, $R^2$, $R^3$ and $R^4$ have the given meanings, and also the physiologically compatible salts thereof, exhibit antiarrhythmic properties and act as inhibitors of the cellular $Na^+/H^+$ antiporter.

6 Claims, No Drawings

4-AMINO-1-PIPERIDYLBENZOYLGUANIDINES

The invention relates to 4-amino-1-piperidylbenzoylguanidines of the formula I

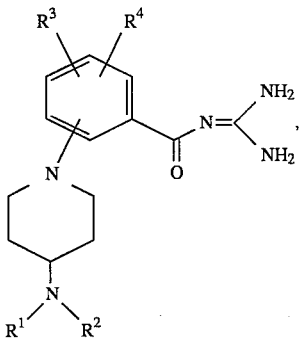

in which $R^1$ and $R^2$ are in each case independent of each other and are H, A, Ph, Ph—alk, CO—A, CO—Ph, CO—Het or an amino protective group known from peptide chemistry, or else $R^1$ and $R^2$ are together also alkylene having from four to five C atoms, where one or two $CH_2$ groups can be replaced by —O—, —S—, —CO—, —NH—, —NA— and/or —N—$CH_2$—Ph, and, where appropriate, a benzene ring can be fused onto the ring formed by $R^1$ and $R^2$ in such a way that a dihydroindolyl radical, a tetrahydroquinolinyl radical, a tetrahydroisoquinolinyl radical or a dihydrobenzimidazolyl radical is present, $R^3$ and $R^4$ are in each case independent of each other and are H, A, Hal, —X—$R^5$, CN, $NO_2$, $CF_3$, $CH_2$—$CF_3$, $SO_n$—$R^7$ or $SO_2$—$NR^5R^6$, $R^5$ is H, A, $CF_3$, $CH_2$—$CF_3$, Ph, Ph—alk, $C_5$–$C_7$-cycloalkyl or $C_5$–$C_7$-cycloalkyl-alk, $R^6$ is H or A, or else $R^5$ and $R^6$ are together also alkylene having from four to five C atoms, where a $CH_2$ group can be replaced by —O—, —S—, —NH—, —NA— or —N—$CH_2$—Ph, $R^7$ is A or Ph, X is O, S or N—$R^6$, A is alkyl having from 1 to 6C atoms, alk is alkylene having from 1 to 4C atoms, Hal is F, Cl, Br or I, Ph is phenyl which is unsubstituted or substituted once, twice or three times by A, OA, Hal, $CF_3$, $NH_2$, NHA or $NA_2$, Het is a saturated or unsaturated five- or six-membered heterocyclic radical having from 1 to 4 N, O and/or S atoms and n is 1 or 2, and the physiologically compatible salts thereof.

An object of the invention was to discover novel compounds having valuable properties, in particular those compounds which can be used for preparing medicaments.

Upon further study of the specification and appended claims, further objects and advantages of this invention will become apparent to those skilled in the art.

It was found that the compounds of the formula I, and their physiologically compatible salts, possess valuable pharmacological properties while being well tolerated physiologically.

The novel compounds are inhibitors of the cellular $Na^+/H^+$ antiporter, i.e. active compounds which inhibit the cellular $Na^+/H^+$ exchange mechanism (Düsing et al., Med. Klin. 87, 378–384 (1982)), and thus represent good antiarrhythmic agents which are particularly suitable for treating arrhythmias which arise as a result of lack of oxygen.

The most well known compound of the acylguanidine group is amiloride. However, this substance first and foremost exhibits hypotensive and saluretic effects, which are undesirable when treating disturbances of cardiac rhythm, in particular, whereas the antiarrhythmic properties are only very weakly expressed.

In addition to this, EP 416,499, for example, discloses compounds which are structurally similar.

In contrast, tile novel substances of the present invention exhibit a good cardioprotective effect and are therefore particularly suitable for the treatment of infarction, for infarction prophylaxis and for treating angina pectoris. In addition, the substances counteract all types of pathological hypoxy and ischaemic damage, so that the disorders which are caused primarily or secondarily by such damage can be treated. The active compounds are also well suited for preventive applications.

Because of the protective effects of these substances in pathological hypoxic or ischaemic situations, there are further possibilities for using these compounds in association with surgical interventions, for protecting organs which are from time to time less well supplied with blood and/or oxygen, in association with organ transplantations, for protecting the organs which are being removed, in association with angioplastic blood vessel or cardiac surgery, in association with ischaemias of the nervous system, in association with therapy of conditions of shock, and for prophylactic prevention of essential hypertension.

In addition, the compounds can also be employed as therapeutic agents in diseases arising from cell proliferation, such as arteriosclerosis, late complications in diabetes, tumor diseases, fibrotic diseases, in particular of the lung, liver and kidneys, and also organ hypertrophies and hyperplasias. In addition to this, these substances are also suitable for diagnosing diseases which are associated with an increased activity of the $Na^+/H^+$ antiporter, e.g. in erythrocytes, thrombocytes or leukocytes.

The effects of the compounds can be ascertained using methods which are known per se, as described, for example, by N. Escobales and J. Figueroa in J. Membrane Biol. 120, 41–49 (1991) or by L. Counillon, W. Scholz, H. L. Land and J. Pouysségur in Mol. Pharmacol. 44, 1041– 1045 (1993).

Examples of suitable experimental animals are mice, rats, guinea pigs, dogs, cats, monkeys or pigs.

The compounds may, therefore, be used as pharmaceutically active compounds in human and veterinary medicine. In addition, they can be used as intermediates for preparing further pharmaceutically active compounds.

In formula I, A is preferably an unbranched alkyl group having 1–6, preferably 1–4, in particular 1, 2 or 3, C atoms, specifically preferably methyl, with ethyl propyl, isopropyl, butyl or isobutyl also being preferred and sec-butyl, tert-butyl, pentyl, isopentyl (3-methylbutyl), hexyl or isohexyl (4-methylpentyl) furthermore being preferred.

If $R^1$ and $R^2$ are together alkylene, the alkylene group is then preferably unbranched, specifically —$(CH_2)_n$— for preference, where n is 4 or 5; however, —$(CH_2)_2$—O—$(CH_2)_2$—, —$(CH_2)_2$—NH—$(CH_2)_2$—, —$(CH_2)_2$—NA—$(CH_2)_2$—, —$CH_2$—O—$(CH_2)_2$—, —$CH_2$—NH—$(CH_2)_2$—, or —$CH_2$—NA—$(CH_2)_2$— or —CO—$(CH_2)_3$—, —CO—$(CH_2)_4$— or —$CH_2$—CO—$(CH_2)_2$ are also preferred.

In addition, the alkylene chain formed by $R^1$ and $R^2$, and whose two ends are bonded to a common N atom, can be linked to a benzene ring in such a way that a dihydroindolyl radical, a tetrahydroquinolinyl radical, a tetrahydroisoquinolinyl radical or a dihydrobenzimidazolyl radical is present.

If $R^1$ and $R^2$ are radicals which are independent of each other, they are then preferably, in each case, hydrogen, A, COA, CO—Ph, CO—2-pyridyl, CO—3-pyridyl or CO—4-pyridyl. Furthermore, compounds of the formula I are preferred in which one of the radicals $R^1$ and $R^2$ is H while the other is an amino protective group which is known per se.

The term "amino protective group" is well known and relates to groups which are suitable for protecting (for blocking) an amino group from chemical reactions, but which can readily be removed once the desired chemical reaction has been carried out at other sites in the molecule. Unsubstituted or substituted acyl groups, aryl groups, aralkoxymethyl groups or aralkyl groups are especially typical of such groups. Their nature and size is otherwise not critical; however, those are preferred which have 1–20, in particular 1–8, C atoms. In connection with the present process, the term "acyl group" is to be interpreted in the widest sense. It encompasses acyl groups which are derived from aliphatic, araliphatic, aromatic or heterocyclic carboxylic acids or sulphonic acids, and also, in particular, alkoxycarbonyl groups, aryloxycarbonyl groups and, in particular, aralkoxycarbonyl groups. Examples of such acyl groups are alkanoyl, such as acetyl, propionyl or butyryl; aralkanoyl, such as phenylacetyl; aroyl, such as benzoyl or toluyl; aryloxyalkanoyl, such as POA (phenoxyacetyl); alkoxycarbonyl, such as methoxycarbonyl, ethoxycarbonyl, 2,2,2-trichloroethoxycarbonyl, BOC (tert-butoxycarbonyl) or 2-iodoethoxycarbonyl; aralkyloxycarbonyl, such as CBZ ("carbobenzoxy"), 4-methoxybenzyloxycarbonyl or FMOC (9-fluorenylmethoxycarbonyl); arylsulphonyl, such as Mtr (4-methoxy-2,3,6-trimethylphenylsulphonyl). Those amino protective groups which are preferred are BOC, and also CBZ, FMOC, benzyl and acetyl.

$R^3$ and $R^4$, in each case independently of each other, are preferably H, A, —$SO_2$—A, —$SO_2$—$NH_2$, —$SO_2$—Ph, Hal, in particular Cl or Br, —O—Ph or o- or p—Cl-phenoxy, or else CN or $CF_3$, particularly preferably —$SO_2CH_3$ and methyl.

The group "—alk" is preferably —$CH_2$— or —$CH_2$—$CH_2$—.

Hal is preferably Cl or Br, while Ph is preferably unsubstituted phenyl or phenyl which is substituted once by Hal, A, OA, $NH_2$, NHA, $NA_2$ or $CF_3$.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl or 2-, 4-, 5-, 6- 7- or 8-quinazolinyl. The heterocyclic radicals can also be partially or completely hydrogenated. Het can therefore also, for example, be 2,3-dihydro-2-, -3-, -4- or-5-furyl, 2,5-dihydro-2-, -3-, -4- or -5-furyl, tetrahydro-2or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro- 1-, -2-, -3-, -4-, -5- or -6-pyridyl, 1,2,3,6-tetrahydro- 1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro- 1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl or 1,2,3,4-tetrahydro-1-, -2-, -3-, -4-, -5-, -6-, -7- or -8-isoquinolinyl.

Accordingly, the invention relates, in particular, to those compounds of the formula I in which at least one of the said radicals has one of the abovementioned, preferred meanings. Some preferred groups of compounds can be expressed by the following formulae Ia to Ih, which conform to the formula I and in which the radicals which are not more precisely described have the meaning given in association with formula I, in which, however, in Ia $R^1$ and $R^2$ are in each case H and $R^3$ is —$SO_2$—$CH_3$, —$SO_2$—$NH_2$ or phenoxy in substituted or unsubstituted form;

in Ib $R^1$ is H, $R^2$ is BOC and $R^3$ or $R^4$ is $SO_2$—$CH_3$, —$SO_2$—$NH_2$ or substituted or unsubstituted phenoxy;

in Ic one of the radicals $R^1$ or $R^2$ is H and the other radical is —CO—Ph, —CO—Het or A;

in Id $R^1$ and $R^2$ are together —$(CH_2)_4$—, —$(CH_2)_5$—, —CO—$(CH_2)_3$—, —CO—$(CH_2)_4$—, —$CH_2$—CO—$(CH_2)_2$—, —$CH_2$—CO—$(CH_2)_3$—, —$(CH_2)_2$—CO—$(CH_2)_2$—, —$(CH_2)_2$—NH—$(CH_2)_2$—, —$(CH_2)_2$—NA—$(CH_2)_2$—, —$(CH_2)_2$—O—$(CH_2)_2$—, —$CH_2$—NH—$(CH_2)_2$—, —$CH_2$—NA— $(CH_2)_2$— or —$CH_2$—O—$(CH_2)_2$—;

in Ie the substituted piperidine group is arranged in the p position in relation to the guanidinecarbonyl group;

in If the substituted piperidine group is in the m position in relation to the guanidinecarbonyl group;

in Ig the substituted piperidine group is in the o position in relation to the guanidinecarbonyl group;

in Ih $R^4$ is $CH_3$ and is in the o position in relation to the guanidinecarbonyl group.

The invention also relates to a process for preparing the compounds of the formula I according to Claim 1, characterized in that a compound of the formula II

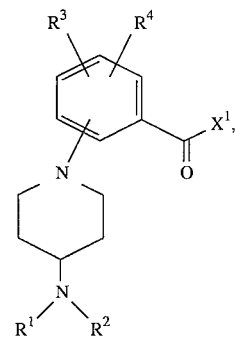

in which $R^1$, $R^2$, $R^3$ and $R^4$ have the previously mentioned meanings, and $X^1$ is Cl, Br, OA, O—CO—A, O—CO—Ph or OH, or another reactive, esterified OK group or leaving group which can readily be substituted nucleophilically, is reacted with guanidine, or in that a benzoylguanidine of the formula III

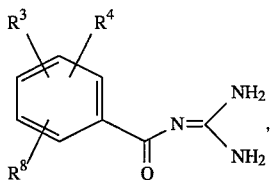

in which $R^3$ and $R^4$ have the previously mentioned meanings, and $R^8$ is F, Cl or $NO_2$, or another group which can be displaced nucleophilically,
is reacted with a piperidine derivative of the formula IV

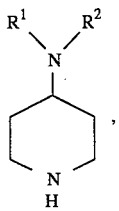

in which $R^1$ and $R^2$ have the given meanings,
or in that a compound which contains one or more reducible group(s) and/or one or more additional C—C and/or C—N bond(s) in place of one or more hydrogen atoms, but which otherwise conforms to the formula I, is treated with a reducing agent,
or in that a compound which contains one or more solvolyzable group(s) in place of one or more hydrogen atoms, but which otherwise conforms to the formula I, is treated with a solvolyzing agent,
and/or in that a base of the formula I which has been obtained is converted into one of its salts by being treated with an acid.

The compounds of the formula I are otherwise prepared by methods which are known per se, as described in the literature (e.g. in the standard works such as Houben-Weyl, Methoden der organischen Chemie (Methods of organic chemistry), Georg-Thieme-Verlag, Stuttgart; Organic Reactions, John Wiley & Sons, Inc., New York; and also in the abovementioned patent application, EP 416,494 and specifically under reaction conditions which are known for the said reactions and which are suitable for these reactions. In this context, use can also be made of variants which are known per se but which have not been mentioned in any detail here.

If desired, the starting compounds may also be formed in situ, such that they are not isolated from the reaction mixture but are instead immediately subjected to further reaction to form the compounds of the formula I.

Preferably, compounds of the formula I are prepared by reacting an activated carboxylic acid derivative of the formula II, where X is particularly preferably Cl or —O—$CH_3$, with guanidine. Reaction variants are particularly suitable in which the free carboxylic acid II ($X^1$=OH) is converted, in a manner known per se, into the particular activated derivative and this derivative is then directly, without intermediate isolation, reacted with guanidine. Examples of methods in which intermediate isolation can be dispensed with are activation with carbonyldiimidazole or dicyclohexylcarbodiimide or the Mukayama variant (Angew. Chem. 91, 788–812 (1979)), with the latter being particularly suitable.

The carboxylic acid of the formula II are preferably prepared by nucleophilic aromatic substitution, proceeding from suitable benzoic acid derivatives, by reaction with corresponding p-substituted piperidines of the formula IV. The reaction is effected in analogy with the reaction of the compound III with the piperidine derivative IV and is described below.

The reaction of a reactive carboxylic acid derivative of the formula II with guanidine is effected in a manner known per se, preferably in a protic or aprotic, polar or non-polar, inert organic solvent.

Suitable solvents for the reaction of the compounds III and IV are mentioned below. However, particularly preferred solvents are methanol, THF, dimethoxyethane, dioxane or mixtures prepared therefrom, and also water. Temperatures of between 20° and the boiling point of the solvent are suitable as the reaction temperature. The reaction times are between 5 min. and 12 hrs. It is expedient to include an acid-capturing agent in the reaction. Any type of base which does not interfere with the reaction itself is suitable for this purpose. However, the use of inorganic bases, such as potassium carbonate, or of organic bases, such as triethylamine or pyridine, or else an excess of the guanidine, is particularly suitable.

Compounds of the formula I can also be prepared by reacting a benzoylguanidine of the formula III with a piperidine of the formula IV. The starting compounds of the formula III can be prepared, in a simple manner, by reacting appropriately substituted benzoic acids, or reactive acid derivatives, such as, for example, acid halides, esters or anhydrides, which can be derived therefrom, with guanidine under reaction conditions which are known per se for amide preparation and which are generally customary.

The piperidines of the formula IV are known per se, as are the methods for preparing them. If they are not known, they can be prepared by the methods which are known per se. Thus, a 4-aminopyridine, for example, can be hydrogenated to give the corresponding 4-aminopiperidine, which can then, if appropriate, be subjected to further reaction to give the different N-substituted 4-aminopiperidines.

In this context, preferred reactions are alkylations and acylations, especially also the introduction of protective groups.

It is furthermore possible to replace the halogen atom in a 4-halopiperidine with a group —$NR^1R^2$—, where $R^1$ and $R^2$ have the given meanings. Reactions with cyclic amines such as pyrrolidine or primary or secondary aromatic amines, such as, for example, aniline, or derivatives derivable therefrom, are particularly preferred.

The preparation of the compound II, and also the reaction of the compound III with a piperidine derivative of the formula IV, are effected in a manner known per se, preferably in a protic or aprotic, polar, inert organic solvent.

For the preparation of II, in the reaction of II with guanidine or in the reaction of III with IV, it is expedient to carry out the reaction in the presence of a base or with an excess of the basic component. Preferred examples of suitable bases are alkali metal or alkaline earth metal hydroxides, carbonates or alcoholates, or organic bases such as triethylamine or pyridine, which can also be used in excess and which can then simultaneously serve as a solvent.

Suitable inert solvents are, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol) or ethylene glycol dimethyl ether (diglyme); ketones, such as acetone or butanone; nitriles, such as acetonitrile; nitro compounds, such as nitromethane or nitrobenzene; esters, such as ethyl acetate or hexamethylphosphoric triamide; sulphoxides, such as dimethyl sulphoxide (DMSO); chlorinated hydrocarbons, such as dichloromethane, chloroform, trichloroethylene, 1,2-dichloroethane or carbon tetrachloride; hydrocarbons, such as benzene, toluene or xylene. In addition to this, mixtures of these solvents with each other are also suitable.

A particularly preferred procedure consists of melting the substances together directly, without adding solvents, at temperatures of between 100° and 400°, particularly preferably at from 100° to 200°.

Derivatives having a primary or secondary amino group ($R^1$ and/or $R^2$=H) are expediently reacted in protected form, irrespective of whether the reaction is carried out in the presence of a solvent or in a melt.

The customary amino protective groups, as used, for example, in peptide chemistry, are suitable for use as protective groups. Examples of some characteristic groups are 2-alkoxy-ethoxy-methyl, such as 2-methoxy-ethoxymethyl (MEM) ("MEM"; can be eliminated, for example, using $ZnBr_2$ or $TiCl_4$ in dichloromethane) or 2-trialkylsilyl-ethoxy-methyl, such as 2-trimethylsilylethoxymethyl (SEM) ("SEM"; can be eliminated, for example, using F ions). Nevertheless, tert-butoxycarbonyl ("BOC"; can be eliminated using $H^+$) is particularly preferred.

Furthermore, one or more of the radicals $R^1$, $R^2$, $R^3$ and/or $R^4$ in a compound of the formula I can be converted into different $R^1$, $R^2$, $R^3$ and/or $R^4$ radicals.

For example, it is possible for a H atom to be replaced by a halogen atom, by means of a halogenation, or by a nitro group, by means of a nitration, and/or for a nitro group to be reduced to an amino group, and/or for an amino group or hydroxyl group to be alkylated or acylated, and/or for a benzyl radical to be eliminated hydrogenolytically (e.g. using $H_2$ on a catalyst such as Pd or using ammonium formate in methanol).

A nitration is achieved under customary conditions, for example using a mixture consisting of concentrated $HNO_3$ and concentrated $H_2SO_4$ at temperatures of between 0° and 30°.

This also applies, in an analogous manner, to halogenation, which can be carried out, for example, using elemental chlorine or bromine in one of the customary, inert solvents, at temperatures of between about 0° and 30°.

A primary or secondary amino group and/or an OH group can be converted into the corresponding secondary or tertiary amino group and/or alkoxy group by treating with alkylating agents. Examples of suitable alkylating agents are compounds of the formulae A—Cl, A—Br or A—I, or corresponding sulphuric acid esters or sulphonic acid esters, such as methyl chloride, methyl bromide, methyl iodide, dimethyl sulphate and methyl p-toluenesulphonate. One or two methyl groups can also be introduced, for example, using formaldehyde in the presence of formic acid. The alkylation is expediently undertaken in the presence or absence of one of the said inert solvents, e.g. DMF, at temperatures of between about 0° and about 120°, it also being possible for a catalyst, preferably a base such as potassium tert-butoxide or NaH to be present.

The halides (e.g. chlorides or bromides) or anhydrides of carboxylic acids of the formula Ac—OH, e.g. acetic anhydride, propionyl chloride, isobutyryl bromide, formic acid/acetic anhydride or benzoyl chloride are expediently suitable for use as acylating agents for acylating amino groups or hydroxyl groups. It is possible to add a base such as pyridine or triethylamine in association with the acylation. The acylation is expediently carried out in the presence or absence of an inert solvent, e.g. of a hydrocarbon, such as toluene, of a nitrile, such as acetonitrile, of an amide, such as DMF, or of an excess of a tertiary base, such as pyridine or triethylamine, at temperatures of between about 0° and 160°, preferably of between 20° and 120°. A formylation is also achieved using formic acid in the presence of pyridine.

A base of the formula I can be converted into the affiliated acid addition salt using an acid. Acids which are suitable for this reaction are those which give rise to physiologically harmless salts. Thus, use can be made of inorganic acid, for example sulphuric acid, nitric acid, hydrohalic acids, such as hydrochloric acid or hydrobromic acid, phosphoric acids, such as orthophosphoric acid, or sulphamic acid, and also of organic acids, in particular aliphatic, alicyclic, araliphatic, aromatic or heterocyclic monobasic or polybasic carboxylic acids, sulphonic acids or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalene monosulphonic and disulphonic acids or laurylsulphuric acid.

The compounds of the formula I and their physiologically harmless salts may be used to produce pharmaceutical preparations, especially by a non-chemical route. When being used for this purpose, they can be brought, together with at least one solid, liquid and/or semiliquid carrier substance or auxiliary substance and, where appropriate, in combination with one or more additional active compound(s), into a suitable dosage The invention furthermore relates to compositions, in particular pharmaceutical preparations, which contain at least one compound of the formula I and/or one of its physiologically compatible salts.

These preparations can be used as medicaments in human or veterinary medicine. Suitable carrier substances are organic or inorganic substances which are suitable for enteral (e.g. oral), parenteral or topical administration and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. For oral applications, use is made, in particular, of tablets coated tablets, capsules, syrups, juices or drops, for rectal application of suppositories, for parenteral application of solutions, preferably oily or aqueous solutions, and also of suspensions, emulsions or implants, and for topical application of ointments, creams, pastes, lotions, gels, sprays, foams, aerosols, solutions (e.g. solutions in alcohols, such as ethanol or isopropanol, acetonitrile, DMF, dimethylacetamide or 1,2-propanediol, or their mixtures with each other and/or with water) or powders. The novel compounds can also be lyophilized and the resulting lyophilizates used, for example, to produce preparations for injection. Liposomal preparations are also especially suitable for topical applications. The given preparations can be sterilized and/or contain auxiliary substances such as glidants, preservatives, stabilizers and/or wetting agents, emulsifiers, salts for influencing the osmotic pressure, buffering substances, coloring substances, flavoring substances and/or aromatizing substances. They can, if desired, also contain one or more additional active compounds, e.g. one or more vitamins.

The compounds of the formula I, and their physiologically compatible salts, can be administered to humans or animals, in particular mammals such as monkeys, dogs, cats, rats or mice, and be used for the therapeutic treatment of the human or animal body and also for controlling diseases, in particular in association with the therapy and/or prophylaxis of disturbances of the cardiovascular system. They are suitable, therefore, for treating arrhythmias, in particular when the latter are caused by a lack of oxygen, angina pectoris, infarctions, ischaemias of the nervous system, such as, for example, stroke or cerebral oedemas, and conditions of shock, and also for preventive treatment.

The substances can also be employed as therapeutic agents in diseases in which cell proliferation plays a role, such as arteriosclerosis, late complications in diabetes, tumor diseases, fibroses and organ hypertrophies and hyperplasias.

In this context, the substances according to the invention are as a rule administered in analogy with known antiarrhythmics, e.g. aprindine, preferably in doses of between about 0.01 and 5 mg, in particular of between 0.02 and 0.5 mg per dosage unit. The daily dose is preferably between about 0.0001 and 0.1, in particular between 0.0003 and 0.01, mg/kg of body weight. However, the special dose for each particular patient depends on a wide variety of factors, for example on the activity of the special compound employed, on the age, on the body weight, on the general state of health, on the sex, on the diet, on the time and route of administration, on the speed of excretion, on the combination of medicines being employed, and on the severity of the particular disease to which the therapy applies. Oral administration is preferred.

In the examples which follow, "customary working-up" denotes:

If required, water is added and extraction takes place using an organic solvent such as ethyl acetate; the organic phase is separated off and dried over sodium sulphate, after which it is filtered and evaporated; the residue is purified by chromatography and/or crystallization.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. P 44 04 183.7, filed Feb. 10, 1994, are hereby incorporated by reference.

EXAMPLES

Example 1

A solution of 550 mg of methyl 3-methylsulphonyl-4-(4-BOC-aminopiperidino)benzoate (m.p. 149°–150°) [obtainable by reacting 3-methylsulphonyl-4-chlorobenzoic acid with 4-BOC-aminopiperidine in a melt and subsequently esterifying the product with methyl iodide/$K_2CO_3$ in dimethylformamide (DMF)] and 383 mg of guanidine in 6 ml of methanol (abs.) is stirred at 60° for a period of 45 min. After removing the solvent, and after customary working-up, N-diaminomethylene-3-methylsulphonyl- 4-(4-BOC-aminopiperidino)benzamide is obtained, m.p. 224°–226°.

The following are obtained in an analogous manner by reacting guanidine with methyl 3-aminosulphonyl-4-(4-BOC-aminopiperidino)benzoate, 3-aminosulphonyl-4-(4-BOC-aminopiperidino)benzoylguanidine;

with methyl 3-methylsulphonyl-4-(4-N,N-dimethylaminopiperidino)benzoate, N-diaminomethylene-3-methylsulphonyl-4-(4-N,N-dimethylaminopiperidino)benzamide; m.p. 249°–252°;

with methyl 3-methylsulphonyl-4-(4-BOC-aminopiperidino)- 5-chlorobenzoate, N-diaminomethylene-3-methylsulphonyl-4-(4-BOC-aminopiperidino)- 5-chlorobenzamide;

with methyl 2-(4-BOC-aminopiperidino)-5-methylsulphonylbenzoate, N-diaminomethylene-2-(4-BOC-aminopiperidino)-5-methylsulphonylbenzamide;

with methyl 3-methylsulphonyl-4-(4-BOC-4-N-methylaminopiperidino)benzoate, N-diaminomethylene-3-methylsulphonyl-4-(4-BOC-4-N-methylaminopiperidino)benzamide;

with methyl 3-(4-BOC-aminopiperidino)-5-methylsulphonylbenzoate, N-diaminomethylene-3-(4-BOC-aminopiperidino)-5-methylsulphonylbenzamide;

with methyl 3-(4-BOC-aminopiperidino)-4-methyl-5-methylsulphonylbenzoate, N-diaminomethylene-3-(4-BOC-aminopiperidino)-4-methyl- 5-methylsulphonylbenzamide;

with methyl 3-(4-BOC-aminopiperidino)-4-methylsulphonylbenzoate, N-diaminomethylene-3-(4-BOC-aminopiperidino)-4-methylsulphonylbenzamide;

with methyl 3-(4-BOC-aminopiperidino)-4-(2-chlorophenoxy)benzoate, N-diaminomethylene-3-(4-BOC-aminopiperidino)-4-(2-chlorophenoxy)benzamide;

with methyl 3-(4-BOC-aminopiperidino)-4-chlorobenzoate, N-diaminomethylene-3-(4-BOC-aminopiperidino)-4-chlorobenzamide;

with methyl 2-methylsulphonyl-4-(4-BOC-aminopiperidino)benzoate, N-diaminomethylene-2-methylsulphonyl-4-(4-BOC-aminopiperidino)benzamide;

with methyl 2-(4-BOC-aminopiperidino)-3-methylsulphonylbenzoate, N-diaminomethylene-2-(4-BOC-aminopiperidino)-3-methylsulphonylbenzamide;

with methyl 3-methylsulphonyl-4-(4-pyrrolidinopiperidino)benzoate, N-diaminomethylene-3-methylsulphonyl-4-(4-pyrrolidinopiperidino)benzamide; m.p. >255°;

with methyl 2-(4-BOC-aminopiperidino)-6-methylsulphonylbenzoate, N-diaminomethylene-2-(4-BOC-aminopiperidino)-6-methylsulphonylbenzamide;

with methyl 3-aminosulphonyl-4-methyl-5-(4-BOC-aminopiperidino)benzoate, 3-aminosulphonyl-4-methyl-5-(4-BOC-aminopiperidino)benzoylguanidine;

with methyl 2-methylsulphonyl-3-(4-BOC-aminopiperidino)benzoate, N-diaminomethylene-2-methylsulphonyl-3-(4-BOC-aminopiperidino)benzamide;

with methyl 2-methylsulphonyl-5-(4-BOC-aminopiperidino)benzoate, N-diaminomethylene-2-methylsulphonyl-5-(4-BOC-aminopiperidino)benzamide;

with methyl 2-(2-chlorophenoxy)-3-(4-BOC-aminopiperidino)benzoate, N-diaminomethylene-2-(2-chlorophenoxy)-3-(4-BOC-aminopiperidino)benzamide;

with methyl 2-(2-chlorophenoxy)-5-(4-BOC-aminopiperidino)benzoate, N-diaminomethylene-2-(2-chlorophenoxy)-5-(4-BOC-aminopiperidino)benzamide;

with methyl 3-(4-BOC-aminopiperidino)-5-(2-chlorophenoxy)benzoate, N-diaminomethylene-3-(4-BOC-aminopiperidino)-5-(2-chlorophenoxy)benzamide;

with methyl 3-methylsulphonyl-4-(4-piperidinopiperidino)benzoate, N-diaminomethylene-3-methylsulphonyl-4-(4-piperidinopiperidino)benzamide: m.p. 255°.

Example 2

1- [1- (4-Diaminomethylenecarbamoyl-2-methylsulphonylphenyl)piperid- 4-yl]-2,3-dihydro-3-methylbenzimidazol- 2-one, from which the corresponding hydrochloride, m.p. 217°–220°, is obtained following treatment with a dilute aqueous solution of HCl, is obtained, in analogy with Example 1, by reaction with guanidine, proceeding from methyl 3-methylsulphonyl-4-[4- (3-N-methyl-2,3-dihydrobenzimidazol- 2-on-1-yl)piperidino]benzoate [obtainable by reacting 3-methylsulphonyl-4-chlorobenzoic acid with 4- (3-N-methyl-2, 3-dihydrobenzimidazol-2-on-1-yl)piperidine in a melt and subsequently esterifying the product with methyl iodide/$K_2CO_3$ in dimethylformamide (DMF)].

The following are obtained in an analogous manner by reacting guanidine
with methyl 3-methylsulphonyl-4-[4-(2-oxopyrrolidino)piperidino]benzoate, N-diaminomethylene-3-methylsulphonyl-4-[4-(2-oxopyrrolidino)piperidino] benzamide.

Example 3

3.4 g of N-diaminomethylene-3-methylsulphonyl-4-(4-BOC-aminopiperidino)benzamide (m.p. 224°–226°) are dissolved in a 2N HCl solution based on dioxane, and this mixture is stirred at room temperature for 1.5 hrs. The crystalline residue is subsequently filtered off with suction and, after washing with dioxane, N-diaminomethylene-3-methylsulphonyl-4-(4-aminopiperidino)benzamide trihydrochloride is obtained, m.p. 232°–240°.

The following are obtained in an analogous manner by removing the BOC protective groups:
from N-diaminomethylene-3-aminosulphonyl-4-(4-BOC-aminopiperidino)benzamide: N-diaminomethylene-3-aminosulphonyl-4-(4-aminopiperidino)benzamide, m.p. 240° (d);
from N-diaminomethylene-3-methylsulphonyl-4-(4-BOC-aminopiperidino)- 5-chlorobenzamide: N-diaminomethylene-3-methylsulphonyl-4-(4-aminopiperidino)- 5-chlorobenzamide dihydrochloride, m.p. 230°;
from N-diaminomethylene-2-(4-BOC-aminopiperidino)-5-methylsulphonylbenzamide: N-diaminomethylene-2-(4-aminopiperidino)-5-methylsulphonylbenzamide dihydrochloride, m.p. 305°–310°;
from N-diaminomethylene-3-(4-BOC-aminopiperidino)-5-methylsulphonylbenzamide: N-diaminomethylene-3-(4-aminopiperidino)-5-methylsulphonylbenzamide;
from N-diaminomethylene-3-(4-BOC-aminopiperidino)-4-methyl- 5-methylsulphonylbenzamide: N-diaminomethylene-3-(4-aminopiperidino)-4-methyl-5-methylsulphonylbenzamide;
from N-diaminomethylene-3-(4-BOC-aminopiperidino)-4-methylsulphonylbenzamide: N-diaminomethylene- 3-(4-aminopiperidino)- 4-methylsulphonylbenzamide dihydrochloride, m.p. 225°;
from N-diaminomethylene-3-(4-BOC-aminopiperidino)-4-(2chlorophenoxy)benzamide: N-diaminomethylene-3-(4-aminopiperidino)-4-(2-chlorophenoxy)benzamide;
from N-diaminomethylene- 3-(4-BOC-aminopiperidino)-4-chlorobenzamide: N-diaminomethylene-3-(4-aminopiperidino)-4-chlorobenzamide;
from N-diaminomethylene-3-methylsulphonyl-4-(4-BOC-4-N-methylaminopiperidino) benzamide: N-diaminomethylene-3-methylsulphonyl-4-(4-N-methylaminopiperidino)benzamide, m.p. 245°–248°;
from N-diaminomethylene-2-methylsulphonyl-4-(4-BOC-aminopiperidino)benzamide: N-diaminomethylene-2-methylsulphonyl-4-(4-aminopiperidino)benzamide;
from N-diaminomethylene-2-(4-BOC-aminopiperidino)-3-methylsulphonylbenzamide: N-diaminomethylene-2-(4-aminopiperidino)-3-methylsulphonylbenzamide;
from N-diaminomethylene-2-(4-BOC-aminopiperidino)-6-methylsulphonylbenzamide: N-diaminomethylene-2-(4-aminopiperidino)-6-methylsulphonylbenzamide;
from N-diaminomethylene-3-aminosulphonyl-4-methyl-5-(4 -BOC-aminopiperidino) benzamide: N-diaminomethylene-3-aminosulphonyl-4-methyl-5-( 4-aminopiperidino)benzamide;
from N-diaminomethylene-2-methylsulphonyl-3-(4-BOC-aminopiperidino)benzamide: N-diaminomethylene-2-methylsulphonyl-3-(4-aminopiperidino)benzamide;
from N-diaminomethylene-2-methylsulphonyl-5-(4-BOC-aminopiperidino)benzamide: N-diaminomethylene-2-methylsulphonyl-5-(4-aminopiperidino)benzamide;
from N-diaminomethylene-2-(2-chlorophenoxy)-3-(4-BOC-aminopiperidino)benzamide: N-diaminomethylene-2-(2-chlorophenoxy)-3-(4-aminopiperidino)benzamide;
from N-diaminomethylene-2-(2-chlorophenoxy)-5-(4-BOC-aminopiperidino)benzamide: N-diaminomethylene-2-(2-chlorophenoxy)-5-(4-aminopiperidino)benzamide;
from N-diaminomethylene-3-(4-BOC-aminopiperidino)-5-( 2-chlorophenoxy)benzamide: N-diaminomethylene-3-(4-aminopiperidino)-5-(2-chlorophenoxy)benzamide.

Example 4

3.9 g of N-diaminomethylene-3-methylsulphonyl- 4-(4-aminopiperidino)benzamide trihydrochloride (m.p. 232°–240°) are dissolved in 50 ml of water, and this solution is adjusted to pH 12 using 1N NaOH and stirred. The precipitate which forms is filtered off with suction, washed with 5 ml of water and dried at 50°. N-Diaminomethylene-3-methylsulphonyl-4-(4-aminopiperidino)benzamide is obtained, m.p. 239°–241°.

Example 5

2.5 g of N-diaminomethylene-3-methylsulphonyl- 4-(4-aminopiperidino)benzamide (m.p. 239°–241°) are suspended in 75 ml of water, and 14.7 ml of 1N HCl are added, while stirring, to this suspension. After removing the solvent and lyophilizing, N-diaminomethylene-3-methylsulphonyl-4-(4-aminopiperidino)benzamide dihydrochloride is obtained, m.p. >260°.

The following are obtained in an analogous manner, proceeding from the corresponding bases
N-diaminomethylene-3-methylsulphonyl-4-(4-N,N-dimethylaminopiperidino)benzamide dihydrochloride, m.p. 198°–206°;
N-diaminomethylene-3-methylsulphonyl-4-(4-piperidinopiperidino)benzamide dihydrochloride, m.p. >250°;
3-aminosulphonyl-4-(4-aminopiperidino)benzoylguanidine dihydrochloride, m.p. 240°;
N-diamino-ethylene-3-methylsulphonyl-4-(4-N-methylaminopiperidino)benzamide dihydrochloride, m.p. >250°;
N-diaminomethylene-3-methylsulphonyl-4-(4-pyrrolidinopiperidino)benzamide dihydrochloride, m.p. >255°.

Example 6

2.1 g of N-diaminomethylene-3-methylsulphonyl- 4-fluorobenzamide [obtainable by reacting methyl 3-methylsulphonyl- 4-fluorobenzoate with guanidine] are melted together, at 150°, with 1.0 g of 4-BOC-aminopiperidine. After a melt period of 1.3 hrs., the mixture is allowed to cool down and the melt cake is dissolved in 10 ml of dichloromethane/methanol. Customary working-up and chromatography on silica gel (ethyl acetate/methanol) give N-diaminomethylene-3-methylsulphonyl-4-(4-BOCaminopiperidino)benzamide, m.p. 225°–226°.

Example 7

1.0 g of 3-methylsulphonyl-4-(4-BOC-aminopiperidino)benzoic acid [obtainable by reacting methyl 3-methylsulphonyl- 4-fluorobenzoate with 4-BOC-aminopiperidine and subsequently hydrolyzing the product to give the free acid] is dissolved in 15 ml of 1-methylpyrrolidone, and 0.67 g of 1-methyl-2-chloropyridinium chloride is added to this solution, which is stirred for 15 min. 0.9 g of guanidinium chloride and 2.6 ml of diisopropylethylamine are then added and the mixture is stirred at room temperature for 1 hr. After customary working-up, and after chromatography on silica gel (flash process, ethylacetate/ 10% methanol), N-diaminomethylene-3-methylsulphonyl- 4-(4-BOC-aminopiperidino)benzamide is obtained.

Example 8

N-Diaminomethylene-3-methylsulphonyl-4-(4-acetamidopiperidino)benzamide hydrochloride, m.p. 199°–203°, is obtained, in analogy with Example 7, by reacting 3-methylsulphonyl-4-(4-acetamidopiperidino)benzoic acid with guanidinium chloride.

The following are obtained in an analogous manner by reaction with guanidinium chloride, proceeding
from 3-methylsulphonyl-4-(4-benzamidopiperidino)benzoic acid, N-diaminomethylene-3-methylsulphonyl-4-(4-benzamidopiperidino)benzamide; m.p. 106°–110°;

from 3-methylsulphonyl-4-[4-(4-pyridylcarboxamido)piperidino] benzoic acid, N-diaminomethylene-3-methylsulphonyl-4-[4-(4-pyridylcarboxamido)piperidino] benzamide;

from 3-methylsulphonyl-4-(4-formamidopiperidino)benzoic acid, N-diaminomethylene-3-methylsulphonyl-4-(4-formamidopiperidino)benzamide;

from 3-methylsulphonyl-4-[3-(4-pyridylcarboxamido)piperidino)benzoic acid, N-diaminomethylene-3-methylsulphonyl-4-[3-(4-pyridylcarboxamido)piperidino] benzamide;

from 3-methylsulphonyl-4-(4-p-chlorobenzamidopiperidino)benzoic acid, N-diaminomethylene-3-methylsulphonyl-4-(4-p-chlorobenzamidopiperidino)benzamide;

from 3-methylsulphonyl-4-[4-(2,4-dimethoxybenzamido)piperidino] benzoic acid, N-diaminomethylene-3-methylsulphonyl-4-[4-(2,4-dimethoxybenzamido)piperidino] benzamide;

from 3-methylsulphonyl-4-[4-(2,4-dichlorobenzamido)piperidino] benzoic acid, N-diaminomethylene-3-methylsulphonyl-4-[4-(2,4-dichlorobenzamido)piperidino] benzamide;

from 3-methylsulphonyl-4-[4-(2-methoxy-4-chlorobenzamido)piperidino] benzoic acid, N-diaminomethylene-3-methylsulphonyl-4-[4-(2-methoxy- 4-chlorobenzamido)piperidino]benzamide.

Example 9

N-Diaminomethylene-2-methyl-4-(4-BOC-aminopiperidino)- 5-methylsulphonylbenzamide is obtained, in analogy with Example 1, by reacting methyl 2-methyl-4-(4-BOC-amidopiperidino)- 5-methylsulphonylbenzoate with guanidine.

The following are obtained in an analogous manner by reacting guanidine
with methyl 2-ethyl-4-(4-BOC-aminopiperidino)-5-methylsulphonylbenzoate, N-diaminomethylene-2-ethyl-4-(4-BOC-aminopiperidino)- 5-methylsulphonylbenzamide;

with methyl 2-trifluoromethyl-4-(4-BOC-aminopiperidino)-5-methylsulphonylbenzoate, N-diaminomethylene-2-trifluoromethyl-4-(4-BOC-aminopiperidino)- 5-methylsulphonylbenzamide;

with methyl 2-chloro-4-(4-BOC-aminopiperidino)-5-methylsulphonylbenzoate, N-diaminomethylene-2-chloro-4-(4-BOC-aminopiperidino)- 5-methylsulphonylbenzamide;

with methyl 2-BOC-amino-4-(4-BOC-aminopiperidino)-5-methylsulphonylbenzoate, N-diaminomethylene-2-BOC-amino-4-(4-BOC-aminopiperidino)- 5-methylsulphonylbenzamide; with methyl 2-cyano-4-(4-BOC-aminopiperidino)-5-methylsulphonylbenzoate, N-diaminomethylene-2-cyano-4-(4-BOC-aminopiperidino)- 5-methylsulphonylbenzamide;

with methyl 2-hydroxy-4-(4-BOC-aminopiperidino)-5-methylsulphonylbenzoate, N-diaminomethylene-2-hydroxy-4-(4-BOC-aminopiperidino)- 5-methylsulphonylbenzamide;

with methyl 3-fluoromethyl-4-(4-BOC-amino piperidino)-5-methyl-sulphonylbenzoate, N-diaminomethylene-3-trifluoromethyl-4-(4-BOC-aminopiperidino)- 5-methylsulphonylbenzamidetrihydrochloride;

with methyl 2-methoxy-4-(4-BOC-aminopiperidino)-5-methylsulphonylbenzoate, N-diaminomethylene-2-methoxy-4-(4-BOC-aminopiperidino)- 5-methylsulphonylbenzamide;

with methyl 3-methylsulphonyl-4-(4-BOC-aminopiperidino)- 5-nitrobenzoate, N-diaminomethylene-3-methylsulphonyl-4-(4-BOC-aminopiperidino)- 5-nitrobenzamide.

Example 10

The following are obtained in analogy with Example 3 by removal of the BOC protective groups, proceeding
from N-diaminomethylene-2-ethyl-4-(4-BOC-aminopiperidino)- 5-methylsulphonylbenzamide: N-diaminomethylene-2-ethyl-4-(4-aminopiperidino)-5-methylsulphonylbenzamide;

from N-diaminomethylene-2-trifluoromethyl-4-(4-BOC-aminopiperidino)- 5-methylsulphonylbenzamide: N-diaminomethylene-2-trifluoromethyl-4-(4-aminopiperidino)- 5-methylsulphonylbenzamide;

from N-diaminomethylene-2-chloro-4-(4-BOC-aminopiperidino)- 5-methylsulphonylbenzamide: N-diaminomethylene-2-chloro-4-(4-aminopiperidino)-5-methylsulphonylbenzamide dihydrochloride, m.p. 302°–305°;

from N-diaminomethylene-2-BOC-amino-4-(4-BOC-aminopiperidino)- 5-methylsulphonylbenzamide: N-diaminomethylene-2-amino-4-(4-aminopiperidino)-5-methylsulphonylbenzamide;

from N-diaminomethylene- 3-trifluoromethyl-4-(4-BOC-aminopiperidino)-benzamide: N-Diaminomethylene-3-trifluoromethyl-4-(4-aminopiperidino)-benzamide trihydrochloride, m.p. 235°;

from N-diaminomethylene -2-methyl-4-(4-BOC-aminopiperidino)- 5-methylsulphonylbenzamide: N-diaminomethylene-2-methyl-4-(4-aminopiperidino)-5-methylsulphonylbenzamide dihydrochloride, m.p. 305°–310°;

from N-diaminomethylene-2-cyano-4-(4-BOC-aminopiperidino)- 5-methylsulphonylbenzamide: N-diaminomethylene-2-cyano-4-(4-aminopiperidino)-5-methylsulphonylbenzamide;

from N-diaminomethylene-2-hydroxy-4-(4-BOC-aminopiperidino)- 5-methylsulphonylbenzamide: N-diaminomethylene-2-hydroxy-4-(4-aminopiperidino)- 5-methylsulphonylbenzamide;

from N-diaminomethylene-2-methoxy-4-(4-BOC-aminopiperidino)- 5-methylsulphonylbenzamide: N-diaminomethylene-2-methoxy- 4-(4-aminopiperidino)- 5-methylsulphonylbenzamide dihydrochloride, m.p. 270°;

from N-diaminomethylene-3-methylsulphonyl-4-(4-BOC-aminopiperidino)- 5-nitrobenzamide: N-diaminomethylene-2-methylsulphonyl-4-(4-aminopiperidino)- 5-nitrobenzamide dihydrochloride, m.p. 264°.

The examples given below relate to pharmaceutical preparations.

Example A: Injection vials

A solution of 100 g of an active compound of the formula I and 5 g of disodium hydrogen phosphate in 3 l of double-distilled water is adjusted to pH 6.5 using 2N hydrochloric acid, sterilized by filtration and used to fill injection vials; the solution in the vials is then lyophilized under sterile conditions and the vials are then sealed in a sterile manner. Each injection vial contains 5 mg of active compound.

Example B: Suppositories

A mixture of 20 g of an active compound of the formula I is melted together with 100 g of soyabean lecithin and 1400 g of cocoa butter and the mixture is poured into molds and allowed to cool. Each suppository contains 20 mg of active compound.

Example C: Solution

A solution is prepared consisting of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 liter and sterilized by irradiation. This solution can be used in the form of eye drops, for example.

Example D: Ointment 500 mg of an active compound of the formula I is mixed with 99.5 g of vaseline under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed, in a customary manner, into tablets such that each tablet contains 10 mg of active compound.

Example F: Coated tablets

Tablets are compressed in analogy with Example E, which tablets are subsequently coated, in a customary manner, with a coating consisting of sucrose, potato starch, talc, gum tragacanth and coloring matter.

Example G: Capsules

Hard gelatine capsules are filled, in a customary manner, with 2 kg of active compound of the formula I such that each capsule contains 20 mg of the active compound.

Example H: Ampoules

A solution of 1 kg of active compound of the formula I in 60 l of double-distilled water is sterilized by filtration and used to fill ampoules; the solution in the ampoules is lyophilized under sterile conditions and the ampoules are sealed in a sterile manner. Each ampoule contains 10 mg of active compound.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 4-amino-1-piperidylbenzoylguanidine of the formula I

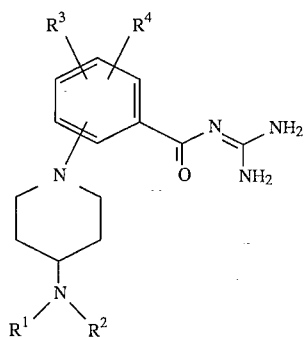

in which $R^1$ and $R^2$ are in each case independent of each other and are H, A, Ph, Ph—alk, CO—A, CO—Ph, CO—Het or an amino protective group known from peptide chemistry, or $R^1$ and $R^2$ are together alkylene having from four to five C atoms, where one or two $CH_2$ groups can be replaced by —O—, —S—, —CO—, —NH—, —NA— and/or N—$CH_2$—Ph, and optionally a phenyl ring can be fused to the ring formed by $R^1$ and $R^2$ such that a dihydroindolyl radical, a tetrahydroquinolinyl radical, a tetrahydroisoquinolinyl radical or a dihydrobenzimidazolyl radical is present, $R^3$ and $R^4$ are in each case independent of each other and are H, A, Hal, —X—$R^5$, CN, $NO_2$, $CF_3$, $CH_2$—$CF_3$, $SO_n$— $R^7$ or $SO_2$—$NR^5R^6$, $R^5$ is H, A, $CF_3$, $CH_2$—$CF_3$, Ph, Ph—alk, $C_5$-$C_7$-cycloalkyl or $C_5$-$C_7$-cycloalkyl-alk, $R^6$ is H or A, or $R^5$ and $R^6$ are together alkylene having from four to five C atoms, where a $CH_2$ group can be replaced by —O—, —S—, —NH—, —NA—, or —N—$CH_2$—Ph, $R^7$ is A or Ph, X is O, S or N—$R^6$, A is alkyl having from 1 to 6 C atoms, alk is alkylene having from 1 to 4 C atoms, Hal is F, Cl, Br or I, Ph is phenyl unsubstituted or substituted once, twice or three times by A, OA, Hal, $CF_3$, $NH_2$, NHA or $NA_2$, Het is a saturated or unsaturated five- or six-membered heterocyclic radical having from 1 to 4 N, O and/or S atoms and n is 1 or 2, or a physiologically compatible salt thereof.

2. (a) N-Diaminomethylene-4-(4-amino-piperidino)-3-methylsulphonylbenzamide;

(b) N-diaminomethylene-4-(4-acetamidopiperidino)-3-methylsulphonylbenzamide;

(c) N-diaminomethylene-4-[4-(2,3-dihydro-2-oxo-3-methylbenzimidazol-1-yl)piperidino]-3-methylsulphonyl benzamide;

(d) N-diaminomethylene-4- (4-tert-butoxycarbonylaminopiperidino)- 3-methylsulphonylbenzamide in accordance with claim 1 or a physiologically compatible salt thereof.

3. A pharmaceutical composition containing at east one compound of the formula I according to claim 1, and/or one of its physiologically compatible salts and a suitable carrier.

4. A method for controlling diseases comprising administering to a patient in need thereof, an effective amount of a compound of the formula I of claim 1, or a physiologically compatible salt thereof.

5. A method for the treatment of arrhythmias, angina pectoris and/or infarction comprising administering to a patient in need thereof an effective amount of a compound of the formula I of claim 1 or a physiologically compatible salt thereof.

6. The compound of claim 1, N-diaminomethylene-2-methyl-4-(4-aminopiperidino)-5-methylsulphonylbenzamide or a physiologically compatible salt thereof.

* * * * *